(12) United States Patent
Itoh

(10) Patent No.: US 7,858,033 B2
(45) Date of Patent: Dec. 28, 2010

(54) SPECIMEN PREPROCESSING/TRANSPORT APPARATUS

(75) Inventor: Teruaki Itoh, Kumamoto (JP)

(73) Assignee: IDS Co., Ltd., Kumamoto (JP)

( * ) Notice: Subject to any disclaimer, the term of this patent is extended or adjusted under 35 U.S.C. 154(b) by 494 days.

(21) Appl. No.: 11/898,846

(22) Filed: Sep. 17, 2007

(65) Prior Publication Data

US 2008/0069730 A1    Mar. 20, 2008

(30) Foreign Application Priority Data

Sep. 20, 2006  (JP)  ............................. 2006-254773

(51) Int. Cl.
*G01N 21/00* (2006.01)
*G01N 31/00* (2006.01)
*G01N 33/00* (2006.01)
*B01L 3/02* (2006.01)

(52) U.S. Cl. ............................. 422/65; 422/63; 422/67; 422/100

(58) Field of Classification Search .................... 422/65
See application file for complete search history.

(56) References Cited

U.S. PATENT DOCUMENTS 6,117,392 A * 9/2000 Hanawa et al. ................ 422/65

2002/0028157 A1 * 3/2002 Takahashi et al. ............. 422/65
2004/0124109 A1 * 7/2004 Hassinen et al. ............. 206/443

FOREIGN PATENT DOCUMENTS

| JP | 7-229904 | 8/1995 |
|---|---|---|
| JP | 9-21814 | 1/1997 |
| JP | 11-304809 | 11/1999 |
| JP | 2002-14109 | 1/2002 |
| JP | 2003-57251 | 2/2003 |
| JP | 2003-302408 | 10/2003 |

* cited by examiner

*Primary Examiner*—In Suk Bullock
*Assistant Examiner*—Jennifer Wecker
(74) *Attorney, Agent, or Firm*—Nixon & Vanderye P.C.

(57) ABSTRACT

A specimen preprocessing/transport apparatus includes a test tube transport path on which test tubes filled with specimens are held in test tube holders and transported, a rack transport path on which sample cups are held in a sample cup rack and the rack is transported, a filled-tube loading section which loads the test tubes into the test tube transport path, a rack loading section which loads the sample cup rack into the rack transport path, an aliquoting/dispensing device which is located in the middle of the test tube transport path and configured to simultaneously aliquot the specimens in the test tubes, and simultaneously dispense the sample cups on the rack transport path, and an analyzer which is located on the downstream side of the rack transport path and configured to receive the sample cup rack stored with the specimens and analyze the specimens.

6 Claims, 7 Drawing Sheets

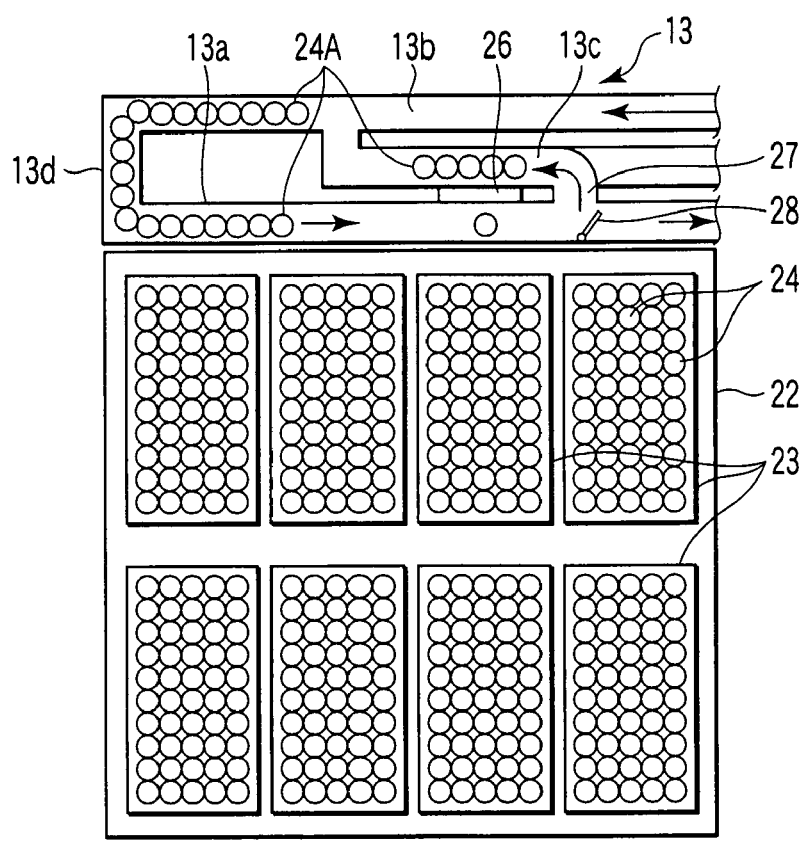
F I G. 3
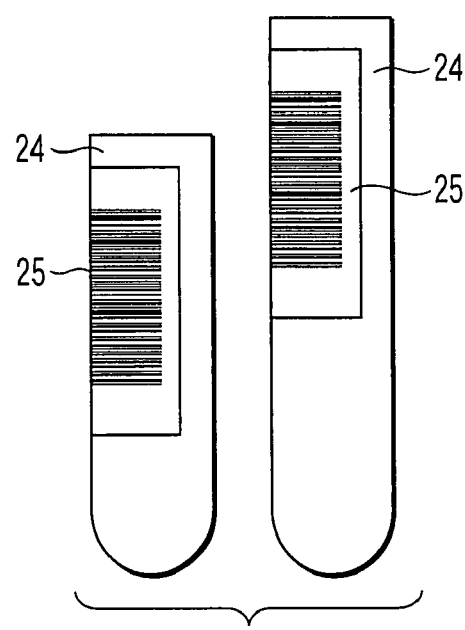
F I G. 4

SPECIMEN PREPROCESSING/TRANSPORT APPARATUS

CROSS-REFERENCE TO RELATED APPLICATIONS

This application is based upon and claims the benefit of priority from prior Japanese Patent Application No. 2006-254773, filed Sep. 20, 2006, the entire contents of which are incorporated herein by reference.

BACKGROUND OF THE INVENTION

1. Field of the Invention

The present invention relates to a specimen preprocessing/transport apparatus for aliquoting blood serum from test tubes stored with a specimen such as blood, dispensing the serum to sample cups, and loading it into an analyzer.

2. Description of the Related Art

A specimen preprocessing/transport apparatus is described in Jpn. Pat. Appln. KOKAI Publication No. 2002-14109 as an example of a known system for loading blood serum from test tubes stored with a specimen, such as blood, into an analyzer. The apparatus described in this patent document comprises a parent-specimen loading unit, an available area detection unit, a stopper removing unit, and a child-specimen container supply unit. The parent-specimen loading unit is located on a specimen operating surface of a desk-type housing. The available area detection unit detects available areas for parent specimens that are fed by the parent-specimen loading unit. The stopper removing unit serves to remove stoppers from specimen containers that contain the parent specimens. The child-specimen container supply unit supplies empty specimen containers for child specimens.

The specimen preprocessing/transport apparatus further comprises a label issuing unit, a dispensing tip supply unit, and a dispensing unit. The label issuing unit prepares identification labels and sticks them on the child-specimen containers supplied from the child-specimen container supply unit. The dispensing tip supply unit supplies disposable dispensing tips. The dispensing unit aliquots the parent specimens in the available areas in the parent-specimen containers, with their stoppers removed by the stopper removing unit, through the dispensing tips supplied from the dispensing tip supply unit and mounted in place. Thereafter, the dispensing unit performs dispensing to the child-specimen containers having the identification labels thereon. The specimen preprocessing/transport apparatus additionally comprises a child-specimen unloading unit and a parent-specimen container unloading unit. The child-specimen unloading unit unloads the child specimens dispensed by the dispensing unit. The parent-specimen container unloading unit unloads the parent-specimen containers after the aliquoting operation.

Thus, a series of processing operations, including the specimen loading and unloading, label issuance, dispensing, etc., is performed entirely automatically, so that there is no possibility of an operator touching the specimens. In consequence, specimen inspection and preprocessing can be automatically executed with a very practical countermeasure against infection.

According to the prior art technique described above, however, complicated parent and child specimen transport units are necessary, and the specimens are loaded into and unloaded one by one from parent and child specimen transport racks, so that the processing efficiency is poor.

The present invention has been made in consideration of these circumstances, and its object is to provide a specimen preprocessing/transport apparatus, in which specimens in specimen-filled test tubes that are transported on a test tube transport path can be efficiently aliquoted and dispensed to sample cups on a rack transport path by an aliquoting/dispensing device located in the middle of the test tube transport path, the respective configurations of the transport paths for the specimen-filled test tubes and the sample cup racks can be simplified, and the processing efficiency can be improved.

BRIEF SUMMARY OF THE INVENTION

According to an aspect of the invention, a specimen reprocessing/transport apparatus comprises a test tube transport path on which test tubes filled with specimens are held individually in test tube holders and transported one by one in a standing position, a rack transport path which extends parallel to the test tube transport path and on which at least five sample cups in each set are held in a sample cup rack in a standing position and the sample cup rack is transported, a filled-tube loading section which loads the specimen-filled test tubes into the test tube transport path; a rack loading section which loads the sample cup rack into the rack transport path, an aliquoting/dispensing device which is located in the middle of the test tube transport path and configured to simultaneously aliquot the specimens in the specimen-filled test tubes, at least five in each set, transported on the test tube transport path, and simultaneously dispense the at least five sample cups on the rack transport path; and an analyzer which is located on the downstream side of the rack transport path and configured to receive the sample cup rack stored with the specimens and analyze the specimens.

According to another aspect of the invention, a specimen preprocessing/transport apparatus comprises, a test tube transport path on which test tubes filled with specimens are held individually in test tube holders and transported one by one in a standing position, a rack transport path which extends parallel to the test tube transport path and on which a plurality of sample cups in each set are held in a sample cup rack in a standing position and the sample cup rack is transported, a filled-tube loading section which loads a plurality of the specimen-filled test tubes having bar-codes thereon into the test tube transport path at a time, a rack loading section which loads the sample cup rack, which holds the plurality of sample cups in a standing position, into the rack transport path, a bar-code reader which is located on that part of the test tube transport path which is situated on the downstream side of the filled-tube loading section and configured to read the bar-codes and sort the specimen-filled test tubes between those test tubes which are requested to be dispensed and those ones which are not, a transport line with dispensing operation and a transport line without dispensing operation which diverge from that part of the test tube transport path which is situated on the downstream side of the bar-code reader and transport the test tubes in a manner such that the test tubes which are and are not requested to be dispensed are distinguishedly distributed at a branching section, an aliquoting/dispensing device which is located in the middle of the transport line with dispensing operation, simultaneously aliquots the specimens in a plurality of the specimen-filled test tubes in each set, transported on the transport line with dispensing operation, and simultaneously dispenses the plurality of sample cups on the rack transport path, an analyzer which is located on the downstream side of the rack transport path, receives the sample cup rack stored with the specimens, and analyzes the specimens; and a rack standby unit which is located on that part of the rack transport path which is situated on the upstream side of the analyzer and controls the rate of loading of the sample cup racks into the analyzer.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a plan view of a filled-tube loading section according to the same embodiment;

FIG. 4 is a front view showing specimen-filled test tubes according to the embodiment;

DETAILED DESCRIPTION OF THE INVENTION

An embodiment of the present invention will now be described with reference to the accompanying drawings.

Figure 1:
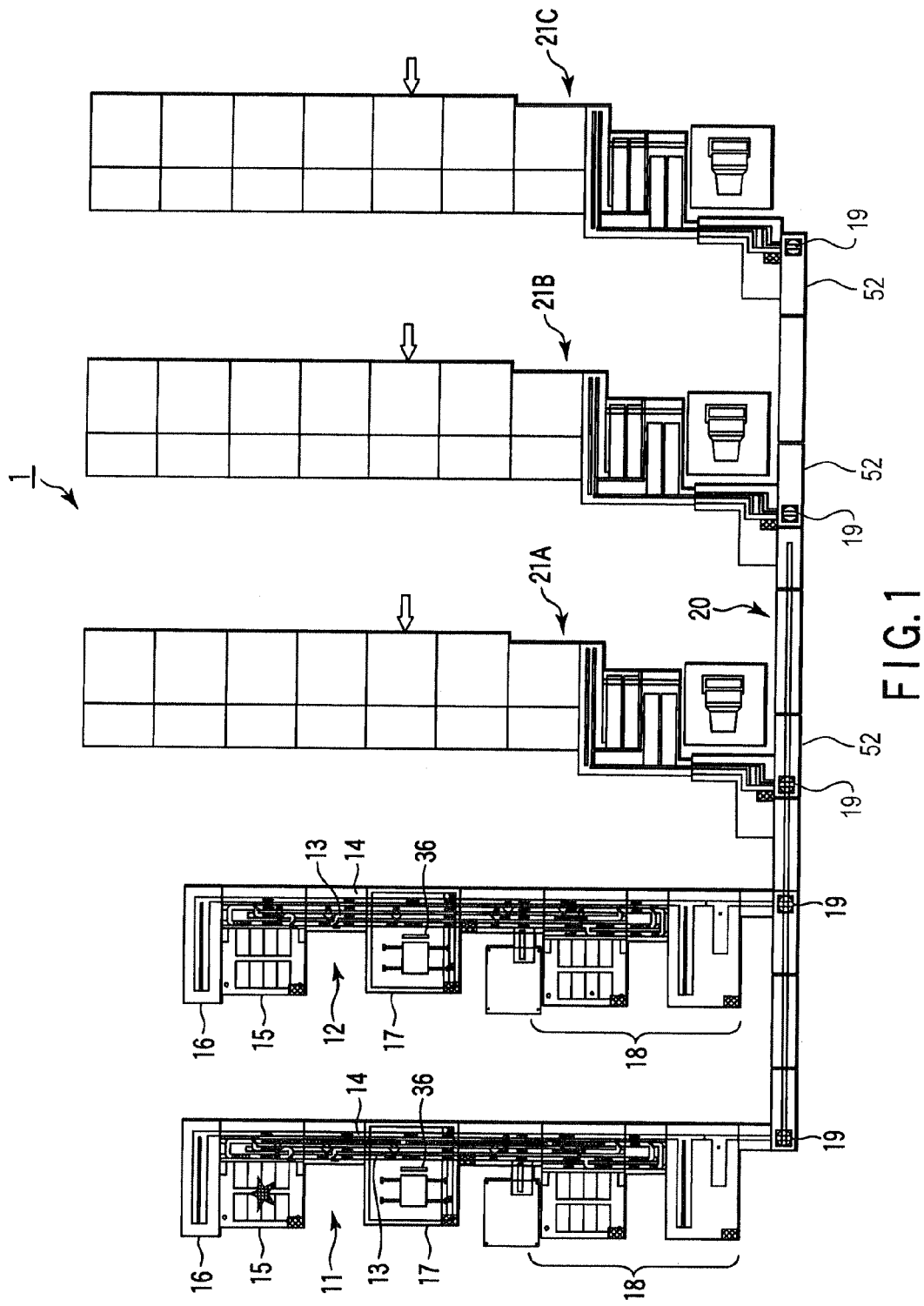
FIG. 1 is a schematic plan view showing a general layout of a specimen preprocessing/transport apparatus according to an embodiment of the present invention.

FIG. 1 is a schematic plan view showing a general layout of a specimen preprocessing/transport apparatus 1 according to the embodiment of the invention. A schematic configuration of the apparatus 1 will be described first. As shown in FIG. 1, a first transport line 11 and a second transport line 12 are arranged parallel to each other. Since the first and second transport lines 11 and 12 are constructed in the same manner, only the first transport line 11 will be described in the following paragraphs. The first transport line 11 includes a test tube transport path 13 and a rack transport path 14, which extend parallel to each other. A test tube loading section 15 for test tubes filled with parent specimens is disposed on the most upstream side of the test tube transport path 13, and a rack loading section 16 on the most upstream side of the rack transport path 14.

An aliquoting/dispensing area 17 and a specimen sorting/unloading area 18 are located in the test tube transport path 13, the former being on the upstream side of the latter. A downstream end of the transport path 13 is connected to a communication path 20 through a transport-direction changing section 19 that extends at right angles to the transport path 13. The communication path 20 is provided with three analyzers 21 (21A, 21B and 21C).

Figure 2:
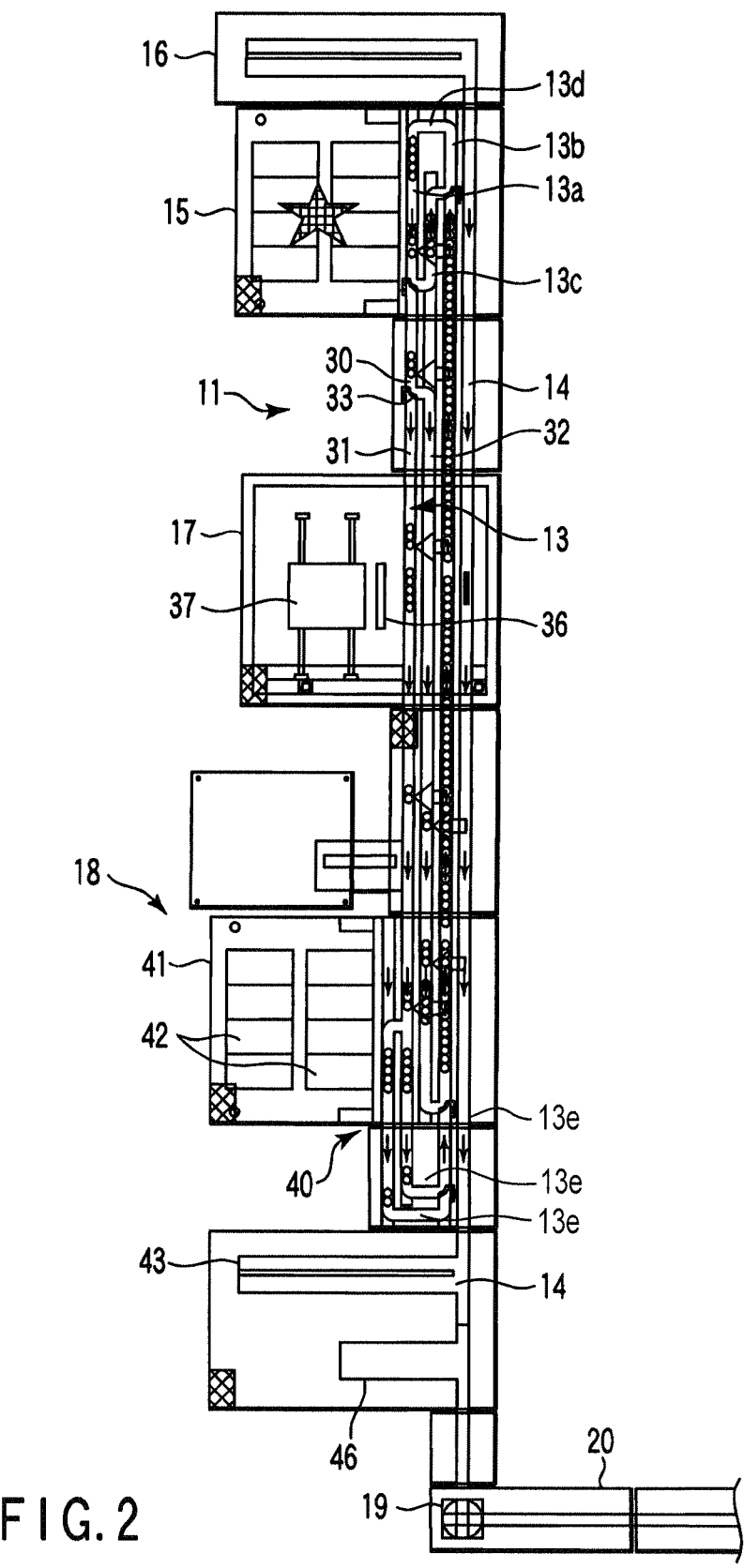
FIG. 2 is a plan view showing a test tube transport path and a rack transport path according to the embodiment.

The following is a specific description of configurations of various parts of the first transport line 11. The test tube transport path 13 of the first transport line 11 shown in FIG. 2 is of a belt-conveyor type, and is provided with an outward path 13a and an inward path 13b, which extend and travel parallel to each other from the upstream side to the downstream side and from the downstream side to the upstream side, respectively. The inward path 13b in the filled-tube loading section 15 is provided with an error line 13c in its middle portion. Further, the most downstream end of the inward path 13b is connected to the upstream end of the outward path 13a by a connecting path 13d.

The following is a description of the filled-tube loading section 15. As shown in FIG. 3, a test tube rack holder section 22 is provided facing a lateral part of the outward path 13a. A plurality of (eight in the present embodiment) test tube racks 23 are located on the holder section 22. Each test tube rack 23 can hold fifty specimen-filled test tubes 24, five in each row and ten in each column, in a standing position. As shown in FIG. 4, the specimen-filled test tubes 24 include two types, 75- and 100-mm types. A label 25 having a bar-code thereon is stuck on a predetermined portion of the side wall of each specimen-filled test tube.

Test tube holders 24A, such as conventional ones described in Jpn. Pat. Appln. KOKAI Publication No. 2003-211006, are set upright on the test tube transport path 13, and the specimen-filled test tubes 24 can be held and transported one by one by them. Specifically, the test tube holders 24A are arranged in a column along the outward path 13a of the test tube transport path 13 so that the specimen-filled test tubes 24 can be transferred from the test tube racks 23 to the holders 24A by a robot arm (not shown). In this case, each five specimen-filled test tubes 24 in each row on the test tube rack 23 are simultaneously set in the test tube holders 24A.

As shown in FIG. 3, a first bar-code reader 26 for reading the bar-codes on the specimen-filled test tubes 24 is provided on a lateral part of the outward path 13a. Further, a branching section 27 between the outward path 13a and an error line 13c is provided with a first gate 28 that discriminates read errors and rejects those specimen-filled test tubes 24 which are erroneously read onto the error line 13c. The error line 13c is filled up when, for example, five specimen-filled test tubes 24 are rejected. If it is full, an operator is warned of it. If the operator is thus warned, he/she manually draws out the specimen-filled test tubes 24 on the error line 13c from the test tube holders 24A and returns them to the test tube rack 23.

Figure 5:
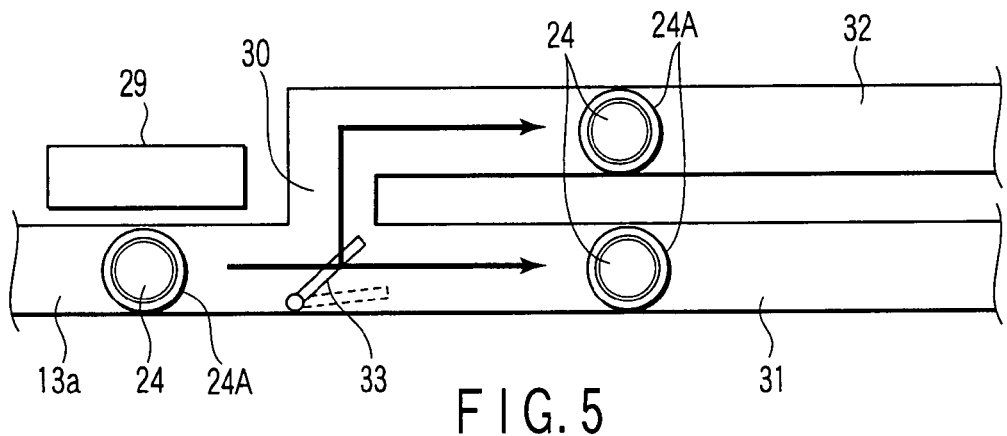
FIG. 5 is a plan view of a branching section between a transport line with dispensing operation and a transport line without dispensing operation according to the embodiment.

As shown in FIGS. 3 and 5, a second bar-code reader 29 that reads the specimen-filled test tubes 24 is provided on that part of the outward path 13a which is situated on the downstream side of the first gate 28. The second bar-code reader 29 distinguishes those test tubes which are requested to be dispensed from those ones which are not. Further, a branching section 30 is provided on the downstream side of the second bar-code reader 29. The outward path 13a is divided at the branching section 30 between a transport line 31 with dispensing operation and a transport line 32 without dispensing operation. The branching section 30 is provided with a second gate 33 that distributes the specimen-filled test tubes 24 between the transport lines 31 and 32 with and without dispensing operation.

Figure 6A:
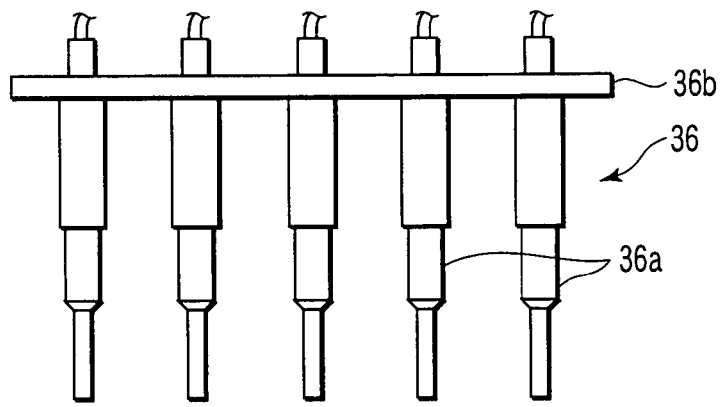
FIG. 6A is a front view of an aliquoting/dispensing device according to the embodiment.
Figure 6B:
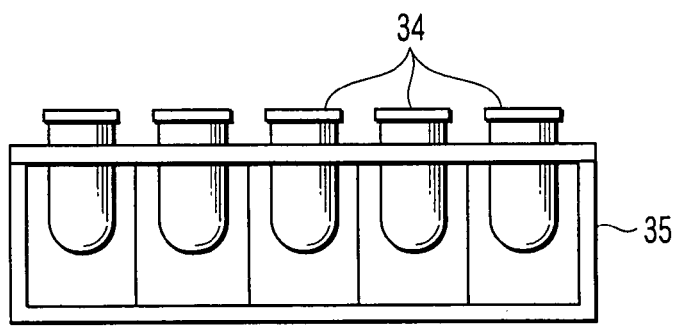
FIG. 6B is a front view of a sample cup rack according to the embodiment.

The transport lines 31 and 32 with and without dispensing operation of the outward path 13a of the test tube transport path 13 extend parallel to each other, and form three transport lines in conjunction with the inward path 13b. Further, the rack transport path 14 is located parallel to the inward path 13b. The rack transport path 14, like the test tube transport path 13, is of a belt-conveyor type. Sample cup racks 35 are kept at the rack loading section 16 on the most upstream side of the path 14. Each sample cup rack 35 holds sample cups 34 as child specimens, e.g., five in each set, in a standing position. As shown in FIG. 6B, the sample cup rack 35 has a rectangular rack body 35a that holds the five sample cups 34, which have substantially the same shape as the specimen-filled test tubes 24. The rack 35 can be transported to the aliquoting/dispensing area 17 through the rack transport path 14.

The aliquoting/dispensing area 17 is provided with a conventional aliquoting/dispensing device 36, such as the one described in Jpn. Pat. Appln. KOKAI Publication No. 2005-233765, facing the outward path 13a. As shown in FIG. 6A, the aliquoting/dispensing device 36 is supported by an elevating holder 36b so that disposable aliquoting/dispensing tips 36a, five in each set, individually face the respective openings of five specimen-filled test tubes 24 in one column. The elevating holder 36b can be raised and lowered by a lifting mechanism (not shown). Thus, when the five specimen-filled test tubes 24 are stopped in a column on the transport line 31 with dispensing operation, a predetermined amount of blood serum is aliquoted from them. The aliquoted serum is dispensed at a time into the sample cups 34, five in each set, through the aliquoting/dispensing tips 36a.

Figure 7:
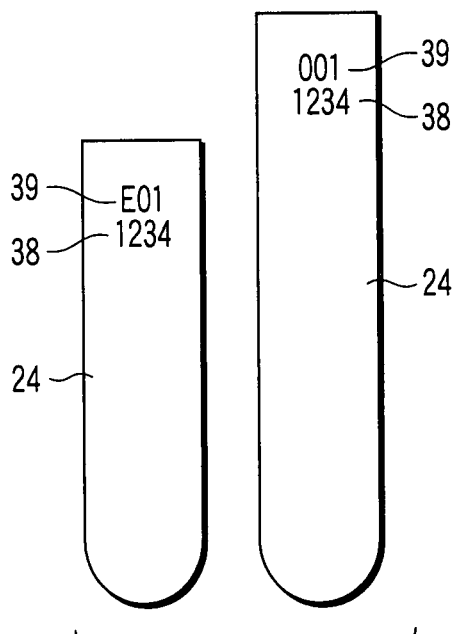
FIG. 7 is a front view showing specimen-filled test tubes according to the embodiment.

An ink jet device 37 is disposed on the downstream side of the aliquoting/dispensing area 17. It serves to print a sequence number (four-digit) 38 and a dispenser serial number (three-digit) 39 on the side wall of each specimen-filled test tube 24, as shown in FIG. 7. In printing the numbers, a nozzle (not shown) is moved toward and away from the transport lines 31 and 32 with and without dispensing operation. If a dispensing error occurs in the aliquoting/dispensing device 36, "E" is added to the dispenser serial number (three-digit) 39.

A defective specimen discharging unit 40 is disposed in the specimen sorting/unloading area 18 on the downstream side of the ink jet device 37. As shown in FIG. 2, it comprises an unloading rack holder section 41 that faces on the outward path 13a and a plurality of test tube racks 42 arranged on the holder section 41. Each test tube rack 42, like each test tube racks 23, can hold fifty specimen-filled test tubes 24, five in each row and ten in each column, in a standing position. Each five specimen-filled test tubes 24 can be simultaneously picked up and transferred from the test tube holders 24A on the transport line 31 with dispensing operation to the test tube rack 42 by a robot arm (not shown). A connecting path 13e that connects the upstream end of the inward path 13b and the respective downstream ends of the transport lines 31 and 32 of the outward path 13a is provided on the downstream side of the defective specimen discharging unit 40.

Figure 8:
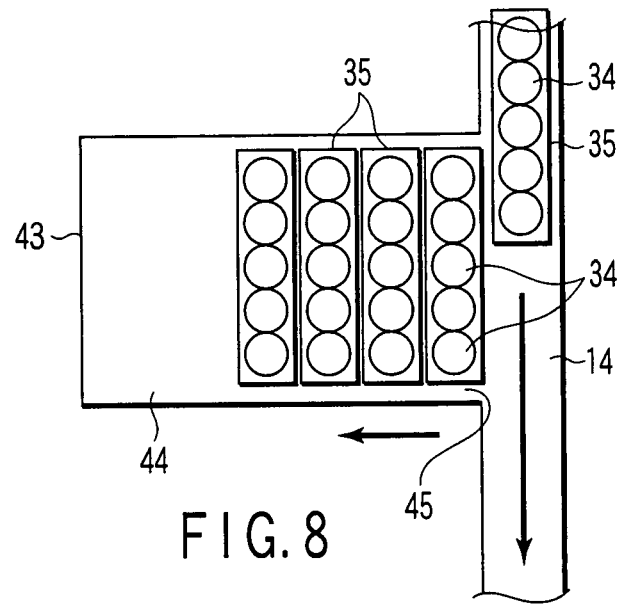
FIG. 8 is a plan view of a rack standby unit according to the embodiment.

Further, the specimen sorting/unloading area 18 is provided with a rack standby unit 43 for controlling the rate of loading into the analyzers 21A, 21B and 21C. As shown in FIG. 8, a rack stocker 44 is located facing the rack transport path 14. It has an opening 45 that opens on the transport path 14, so that the sample cup racks 35 that are transported along the path 14 can be moved in a transverse direction (perpendicular to the transport direction) to be stored in the rack stocker 44. Thus, when the analyzers 21A, 21B and 21C are full, the sample cup racks 35 can be temporarily evacuated to control the rate of loading into the analyzers.

Figure 9:
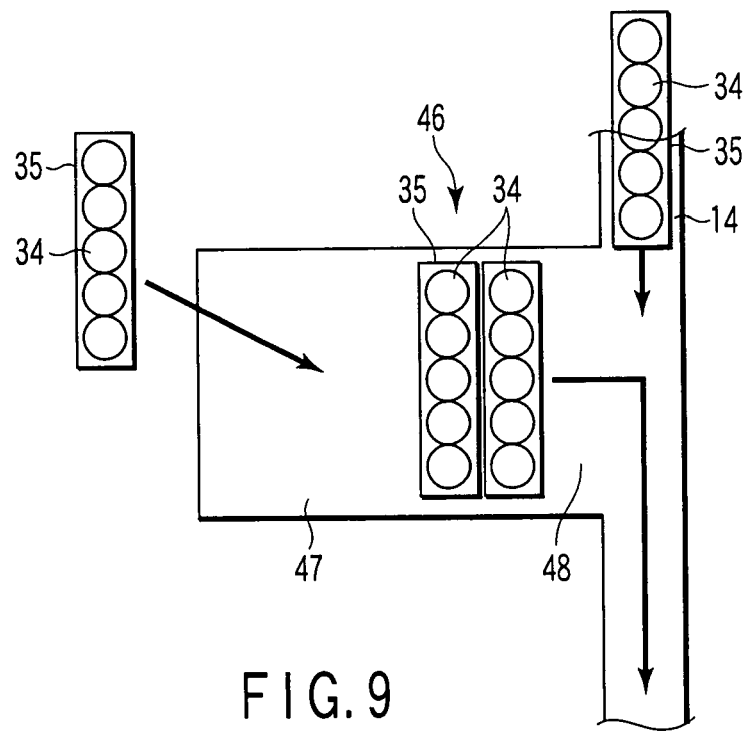
FIG. 9 is a plan view of a rack interrupt loading unit according to the embodiment.

A rack interrupt-loading unit 46 is provided in that part of the rack transport path 14 which is located on the downstream side of the rack standby unit 43. As shown in FIG. 9, the unit 46 is provided with a loading stocker 47 that faces on the rack transport path 14. The loading stocker 47 has an opening 48 that opens on the transport path 14, so that the sample cup racks 35 that are stored with the sample cups 34 dispensed by means of a backup machine or the like after manual dispensing can be manually put into the stocker 47. The sample cup racks 35 can be loaded in an interruptive manner into the rack transport path 14 through the opening 48 of the loading stocker 47.

Figure 10:
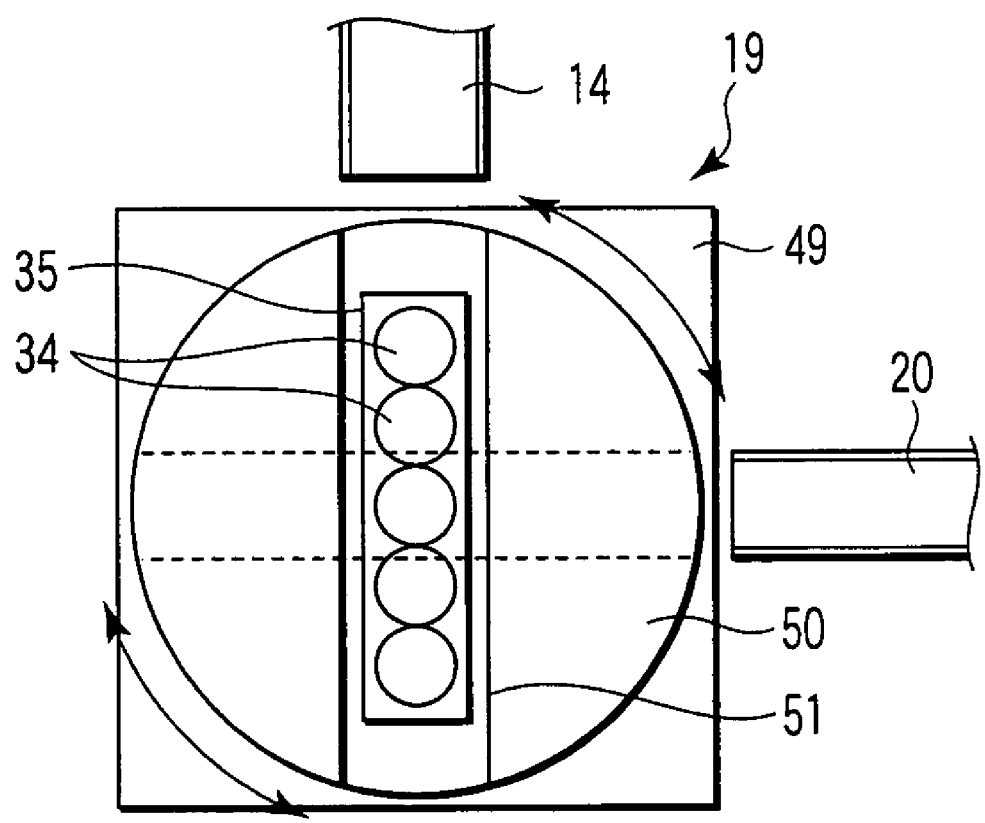
FIG. 10 is a plan view of a transport-direction changing section according to the embodiment.
Figure 11:
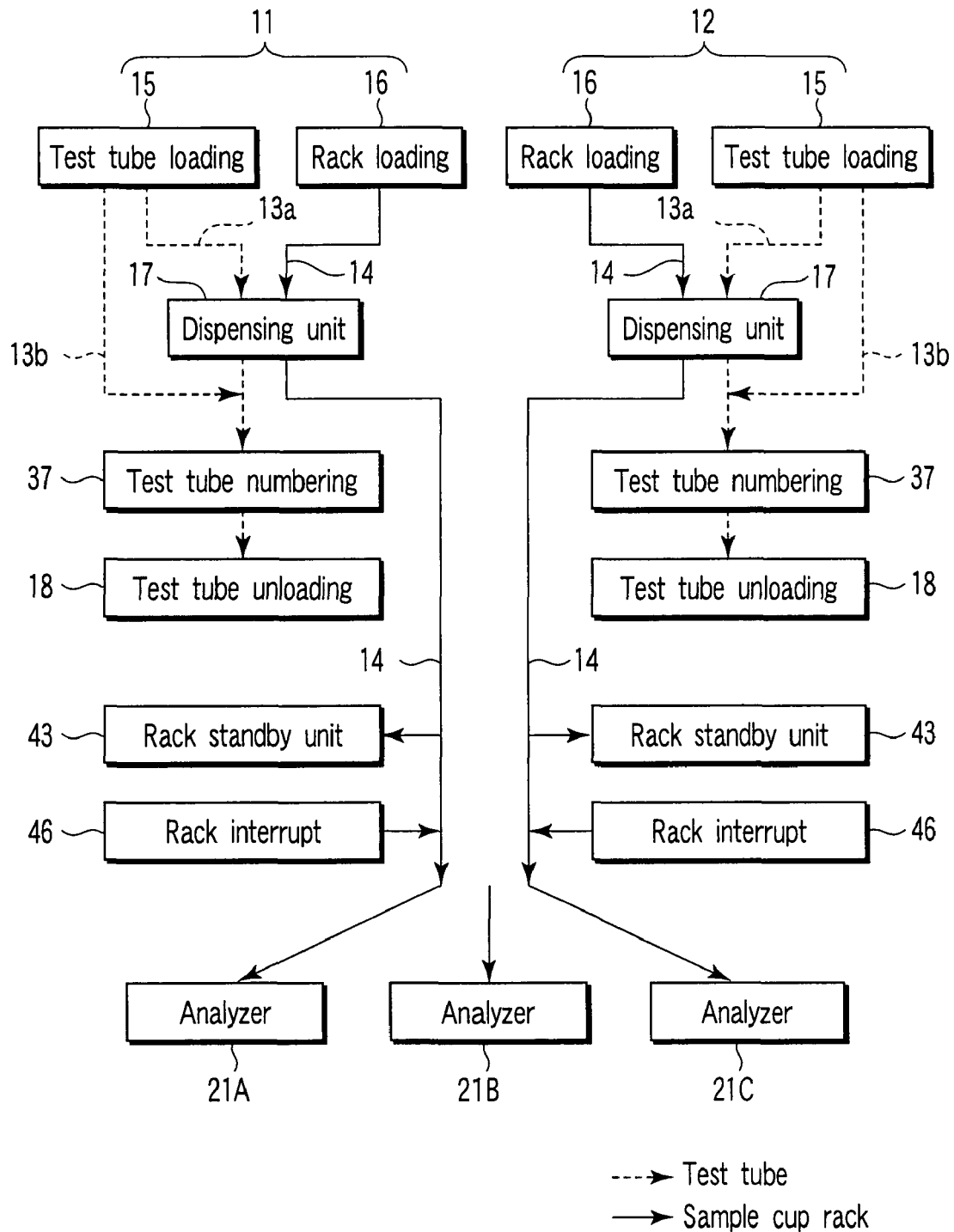
FIG. 11 is a block diagram showing the operation of the specimen preprocessing/transport apparatus according to the embodiment.

As shown in FIG. 10, the transport-direction changing section 19 that perpendicularly connects the communication path 20 and the downstream end of the rack transport path 14 is provided with a turntable 50 that can reversibly rotate through at least 90 degrees with respect to a base 49. A rail 51 is provided extending diametrically in the central part of the turntable 50, so that each sample cup rack 35 from the rack transport path 14 can be kept on the rail 51 as it is redirected toward the communication path 20 by rotating the turntable 50 through 90 degrees. Equivalents of the turntable 50, which can reversibly rotate through 90 degrees at the transport-direction changing section 19, are provided individually at branching sections 52 that connect the communication path 20 and the analyzers 21A, 21B and 21C.

The following is a description of the operation of the specimen preprocessing/transport apparatus 1 constructed in this manner.

In the present embodiment, the first and second transport lines 11 and 12 are actuated simultaneously, and the specimen-filled test tubes 24 supported by the test tube holders 24A are transported through the respective test tube transport paths 13 of the transport lines 11 and 12. Further, the sample cups 34 supported by the sample cup racks 35 are transported through the rack transport path 14. The sample cup racks 35, which have the sample cups 34 transported from the first and second transport lines 11 and 12, are transported to the analyzers 21A, 21B and 21C through the communication path 20, whereupon the specimens are analyzed.

Since the first and second transport lines 11 and 12 operate in the same manner, only the operation of the first transport line 11 will be described below. Each five specimen-filled test tubes 24 that are arranged in a row in each test tube rack 23e are simultaneously grasped and loaded into the outward path 13a of the test tube transport path 13 by the robot arm. Since the test tube holders 24A are held on standby on the outward path 13a as this is done, the five specimen-filled test tubes 24 are set individually in the holders 24A and transported on the outward path 13a.

Since the bar-coded label 25 is stuck on each specimen-filled test tube 24, the bar-code is read by the bar-code reader 26. If any bar-code or bar-codes fail to be read by the reader 26 or if a read error occurs, the first gate 28 is actuated to reject the specimen-filled test tube or tubes 24 concerned onto the error line 13c. The specimen-filled test tubes 24 read by the bar-code reader 26 pass through the branching section 27 of the outward path 13a. The bar-codes are read by the second bar-code reader 29, which is located on the downstream side of the branching section 27, and the specimen-filled test tubes 24 are distributed by the second gate 33 between those test tubes which are requested to be dispensed and those ones which are not.

Those specimen-filled test tubes 24 which are requested to be dispensed are transported to the aliquoting/dispensing area 17 through the transport line 31 with dispensing operation. Those ones which are not are transported through the transport line 32 without dispensing operation. On the other hand, the sample cup racks 35 that support the sample cups 34 are transported from the rack loading section 16 of the rack transport path 14 and loaded into the aliquoting/dispensing area 17.

The aliquoting/dispensing tips 36a, five in each set, of the aliquoting/dispensing device 36 that is located facing the outward path 13a of the aliquoting/dispensing area 17 aliquot a predetermined amount of blood serum from the five specimen-filled test tubes 24 on the transport line 31 with dispensing operation. The aliquoted serum is simultaneously dispensed to the five sample cups 34 in each set on the rack transport path 14 by the aliquoting/dispensing tips 36a. When the dispensing is completed, the five sample cups 34 are transported to specimen sorting/unloading area 18 with the aid of the sample cup rack 35.

When the specimen-filled test tubes 24 are transported through the transport line 31 with dispensing operation and reach the ink jet device 37 on the downstream side of the aliquoting/dispensing area 17 after the completion of the dispensing, the ink jet device 37 prints the sequence number (four-digit) 38 and the dispenser serial number (three-digit) 39 on the side wall of each specimen-filled test tube 24. As this is done, the nozzle is also moved toward and away from the transport line 32 without dispensing operation to number the specimen-filled test tubes 24.

After the completion of the dispensing, each five specimen-filled test tubes 24 of each lot are picked up and transferred from the test tube holders 24A on the transport line 31 with dispensing operation to the test tube rack 42 by the robot arm (not shown). Since the transport lines 31 and 32 with and without dispensing operation are connected to the inward path 13b by the connecting path 13e, moreover, the test tube holders 24A are returned to the upstream side through the inward path 13b.

After the aliquoting/dispensing is completed, furthermore, the sample cup racks 35, which each have the five sample cups 34 in each set and are transported on the rack transport path 14, are loaded into the analyzers 21A, 21B and 21C. If the analyzers 21A, 21B and 21C are full, the sample cup racks 35 that are transported along the rack transport path 14 are moved in the transverse direction (perpendicular to the transport direction) to be stored in the rack stocker 44 for temporary evacuation or refuge. Thus, the rate of loading into the analyzers 21A, 21B and 21C can be controlled.

After manual dispensing, the sample cup racks 35 that are stored with the sample cups 34 dispensed by means of the backup machine or the like are manually put into the loading stocker 47 of the rack interrupt-loading unit 46 on the downstream side of the rack standby unit 43. Then, the sample cup racks 35 can be loaded in an interruptive manner into the rack transport path 14 through the opening 48 of the loading stocker 47.

Thus, while the parent specimen-filled test tubes 24 are being transported along the test tube transport path 13, blood serum is automatically aliquoted by the aliquoting/dispensing device 36 and dispensed to the sample cups 34. The serum dispensed to the sample cups 34 is loaded into the analyzers 21A, 21B and 21C by the sample cup racks 35 and analyzed therein. The aliquoting/dispensing device 36 uses its five aliquoting/dispensing tips 36a to aliquot a predetermined amount of serum from the five specimen-filled test tubes 24, and the aliquoted serum is dispensed simultaneously to the five sample cups 34 in each set by the aliquoting/dispensing tips 36a. However, the test tubes and the sample cups in each set are not limited to this number, but their number may be any other suitable one. Preferably, the number should be five or more.

According to the specimen preprocessing/transport apparatus 1 of the present embodiment, the aliquoting/dispensing device 36 that is located in the middle of the test tube transport path 13 can simultaneously aliquot the specimens in the specimen-filled test tubes, at least five in each set, transported on the test tube transport path 13, and simultaneously dispense them to the at least five sample cups 34 on the rack transport path 14, so that the processing can be performed efficiently. Further, the respective configurations of the transport paths for the specimen-filled test tubes 24 and the sample cup racks 35 can be simplified, and the processing efficiency can be improved.

By simultaneously actuating the first and second transport lines 11 and 12, moreover, the loading rate can be controlled depending on the processing capacities of the analyzers 21A, 21B and 21C, so that the processing capacities can be enhanced.

The present invention is not limited directly to the embodiment described above, and its components may be embodied in modified forms without departing from the scope or spirit of the invention. Further, various inventions may be made by suitably combining a plurality of components described in connection with the foregoing embodiment. For example, some of the components according to the foregoing embodiment may be omitted. Furthermore, components according to different embodiments may be combined as required.

What is claimed is:

1. A specimen preprocessing/transport apparatus comprising:
   a test tube transport path on which test tubes filled with specimens are held individually in test tube holders and transported one by one in a standing position;
   a rack transport path which extends parallel to the test tube transport path and on which at least five sample cups in each set are held in a sample cup rack in a standing position and the sample cup rack is transported;
   a filled-tube loading section which loads the specimen-filled test tubes into the test tube transport path, the filled-tube loading section being located on a most upstream side of the test tube transport path;
   a rack loading section which loads the sample cup rack into the rack transport path, the rack loading section being located on a most upstream side of the rack transport path;
   an aliquoting/dispensing device which is located in the middle of the test tube transport path and configured to simultaneously aliquot the specimens in the specimen-filled test tubes, at least five in each set, transported on the test tube transport path, and simultaneously dispense the at least five sample cups on the rack transport path;
   an analyzer which is located on the downstream side of the rack transport path and configured to receive the sample cup rack stored with the specimens and analyze the specimens;
   a rack standby unit which is located on that part of the rack transport path which is situated on the upstream side of the analyzer and controls the rate of loading of the sample cup racks into the analyzer; and
   a rack interrupt-loading unit which is located on a more downstream side of the rack transport path than the rack standby unit and interrupts the rack transport path to load the sample cup rack into the rack transport path.

2. A specimen preprocessing/transport apparatus comprising:

a test tube transport path on which test tubes filled with specimens are held individually in test tube holders and transported one by one in a standing position;

a rack transport path which extends parallel to the test tube transport path and on which a plurality of sample cups in each set are held in a sample cup rack in a standing position and the sample cup rack is transported;

a filled-tube loading section which loads a plurality of the specimen-filled test tubes having bar-codes thereon into the test tube transport path at a time, the filled tube loading section being located on a most upstream side of the test tube transport path;

a rack loading section which loads the sample cup rack, which holds the plurality of sample cups in a standing position, into the rack transport path, the rack loading section being located on a most upstream side of the rack transport path;

a bar-code reader which is located on that part of the test tube transport path which is situated on the downstream side of the filled-tube loading section and configured to read the bar-codes and sort the specimen-filled test tubes between those test tubes which are requested to be dispensed and those ones which are not;

a transport line with dispensing operation and a transport line without dispensing operation which diverge from that part of the test tube transport path which is situated on the downstream side of the bar-code reader and transport the test tubes in a manner such that the test tubes which are and are not requested to be dispensed are distinguishedly distributed at a branching section;

an aliquoting/dispensing device which is located in the middle of the transport line with dispensing operation, simultaneously aliquots the specimens in a plurality of the specimen-filled test tubes in each set, transported on the transport line with dispensing operation, and simultaneously dispenses the plurality of sample cups on the rack transport path;

an analyzer which is located on the downstream side of the rack transport path, receives the sample cup rack stored with the specimens, and analyzes the specimens;

a rack standby unit which is located on that part of the rack transport path which is situated on the upstream side of the analyzer and controls the rate of loading of the sample cup racks into the analyzer; and a rack interrupt-loading unit which is located on a more downstream side of the rack transport path than the rack standby unit and interrupts the rack transport path to load the sample cup rack into the rack transport path.

3. A specimen preprocessing/transport apparatus according to claim 1, wherein the test tube transport path is a belt conveyor which transports the test tube holders, which hold the specimen-filled test tubes in a standing position, and comprises an outward path having the filled-tube loading section, an inward path extending parallel to the outward path, and connecting paths which connect respective upstream and downstream ends of the outward path and the inward path, and wherein the empty test tube holders from which the specimen-filled test tubes are picked up are returned to the filled-tube loading section through the inward path.

4. A specimen preprocessing/transport apparatus according to claim 1, wherein the test tube transport path, which transports the specimen-filled test tubes in the test tube holders one by one in a standing position, and the rack transport path, which transports the plurality of sample cups in each set held in the sample cup rack in a standing position, linearly extend parallel to each other, and the aliquoting/dispensing device and the rack standby unit are located facing the test tube transport path and the rack transport path.

5. A specimen preprocessing/transport apparatus according to claim 2, wherein the test tube transport path is a belt conveyor which transports the test tube holders, which hold the specimen-filled test tubes in a standing position, and comprises an outward path having the filled-tube loading section, an inward path extending parallel to the outward path, and connecting paths which connect respective upstream and downstream ends of the outward path and the inward path, and wherein the empty test tube holders from which the specimen-filled test tubes are picked up are returned to the filled-tube loading section through the inward path.

6. A specimen preprocessing/transport apparatus according to claim 2, wherein the test tube transport path, which transports the specimen-filled test tubes in the test tube holders one by one in a standing position, and the rack transport path, which transports the plurality of sample cups in each set held in the sample cup rack in a standing position, linearly extend parallel to each other, and the aliquoting/dispensing device and the rack standby unit are located facing the test tube transport path and the rack transport path.

* * * * *